(12) United States Patent
Van Griffin et al.

(10) Patent No.: US 7,901,370 B1
(45) Date of Patent: Mar. 8, 2011

(54) POLYMERIC SPLINT AND RAPID-SETTING POLYURETHANE

(75) Inventors: Lanny Van Griffin, Arroyo Grande, CA (US); Dane Robert Jones, Los Osos, CA (US)

(73) Assignee: California Polytechnic Corporation, San Luis Obispo, CA (US)

( * ) Notice: Subject to any disclaimer, the term of this patent is extended or adjusted under 35 U.S.C. 154(b) by 654 days.

(21) Appl. No.: 11/201,831

(22) Filed: Aug. 10, 2005

(51) Int. Cl.
*A61F 5/00* (2006.01)

(52) U.S. Cl. ............................................................ 602/8

(58) Field of Classification Search .................. 602/4–9, 602/41

See application file for complete search history.

(56) References Cited

U.S. PATENT DOCUMENTS

| | | | |
|---|---|---|---|
| 3,375,822 A * | 4/1968 | Rose | 602/8 |
| 4,427,002 A * | 1/1984 | Baron et al. | 602/8 |
| 4,537,184 A * | 8/1985 | Williams, Jr. | 602/8 |
| 4,627,424 A * | 12/1986 | Baron et al. | 602/8 |
| 5,480,376 A * | 1/1996 | Duback et al. | 602/8 |
| 6,030,355 A * | 2/2000 | Callinan et al. | 602/6 |
| 6,475,502 B1 * | 11/2002 | Lee et al. | 424/405 |
| 6,624,211 B2 * | 9/2003 | Karim et al. | 523/116 |

* cited by examiner

*Primary Examiner* — Michael A. Brown
(74) *Attorney, Agent, or Firm* — Martine Penilla & Gencarella, LLP (57) ABSTRACT

A splint includes a first container capable of being wrapped about an item to be supported and a second container capable of containing a multiple part mixture during a mixing operation. The second container being capable of delivering the mixture into the first container, wherein the mixture hardens to form a support structure. A method for using the splint is also disclosed.

7 Claims, 8 Drawing Sheets

POLYMERIC SPLINT AND RAPID-SETTING POLYURETHANE

The present invention relates generally to splinting and more particularly, to methods and systems for using a rapid-hardening splint.

SUMMARY

Broadly speaking, the present invention fills these needs by providing an improved splint and an improved, rapid-setting polyurethane. It should be appreciated that the present invention can be implemented in numerous ways, including as a process, an apparatus, a system, computer readable media, or a device. Several inventive embodiments of the present invention are described below.

One embodiment provides a splint that includes a first container capable of being wrapped about an item to be supported and a second container capable of containing a multiple part mixture during a mixing operation. The second container being capable of delivering the mixture into the first container, wherein the mixture hardens to form a support structure.

The hardened mixture can have a hardness of from about 60 to about 85 Shore A. The mixture can include a polymer. The mixture can include a polyurethane capable of setting in less than about five minutes.

The second container can be incorporated into the first container. The second container can be separate from the first container. The second container can be removably coupled to the first container.

Another embodiment provides a method of using a splint. The method includes mixing a plurality of polyurethane components in a 2-chambered container, placing the mixture into the splint, wrapping the splint about an item to be supported by the splint and holding the splint in place until the mixture hardens.

Placing the mixture into the splint can include applying pressure on the 2-chambered container to cause the mixture to flow from the 2-chambered container and into the splint. The splint can include a first container capable of being wrapped about the item to be supported and a second container capable of containing the mixture during a mixing operation. The second container being capable of delivering the mixture into the first container. The mixture hardens to form a support structure.

Yet another embodiment provides a rapid-setting polyurethane. The rapid setting polyurethane includes an isocyanate prepolymer as a first part of a 2-part mixture and an orthophthalate-diethylene glycol based aromatic polyester polyol, glycerol, and 2,2,4-trimethyl-1,3-pentanediol monoisobutyrate as a second part of the 2-part mixture.

The rapid-setting polyurethane has a hardness rated at Shore A 80-85 with a high density foam of about 0.4 g/cc. The first part can be based on polymeric 4,4'-methylene bisphenylisocyanate, ethylenediamine tetrakis (propoxylate-block-ethoxylate) tetrol and 2,2,4-trimethyl-1,3-pentanedioldiisobutyrate. The rapid-setting polyurethane can cure in less than about five minutes. The rapid-setting polyurethane can cure with a film thickness of less than about 1/8 inch.

Other aspects and advantages of the invention will become apparent from the following detailed description, taken in conjunction with the accompanying drawings, illustrating by way of example the principles of the invention.

BRIEF DESCRIPTION OF THE DRAWINGS

The present invention will be readily understood by the following detailed description in conjunction with the accompanying drawings.

DETAILED DESCRIPTION

Several exemplary embodiments for an improved splint and an improved, rapid-setting polyurethane will now be described. It will be apparent to those skilled in the art that the present invention may be practiced without some or all of the specific details set forth herein.

The Polymeric Splint (PAL—polymeric arm and leg) is a completely self-contained splinting system. The splint will form a rigid and strong conforming outer structure to immobilize a fractured extremity. The device will function under austere conditions with a minimum of training. The device is light weight with a small volume. The splint could also be used for other applications, such as forming a "sugar tong" splint, a neck brace, managing humeral fractures, fractures to the foot-anlde complex, or tibial shaft fractures.

One embodiment provides a new, self-contained, splinting system for use in tactical environments that is lightweight, rigid, strong, and easily applied. It is envisioned that advanced composite materials will be used such that the construct will be light, thin, and stiff.

Figure 1:
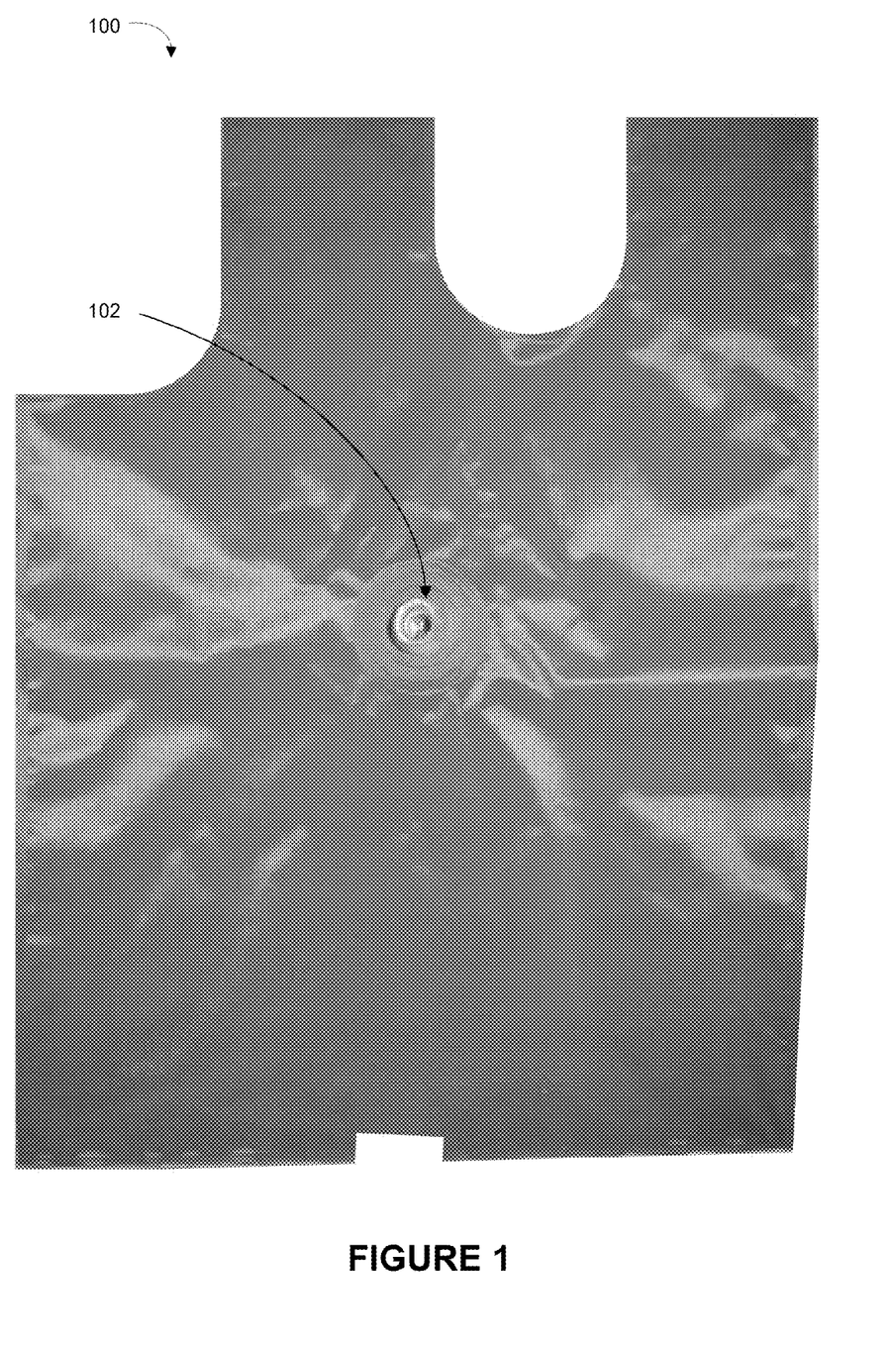
FIG. 1 is a prototype design for rapid setting polymer splint, in accordance with one embodiment of the present invention.
Figure 2:
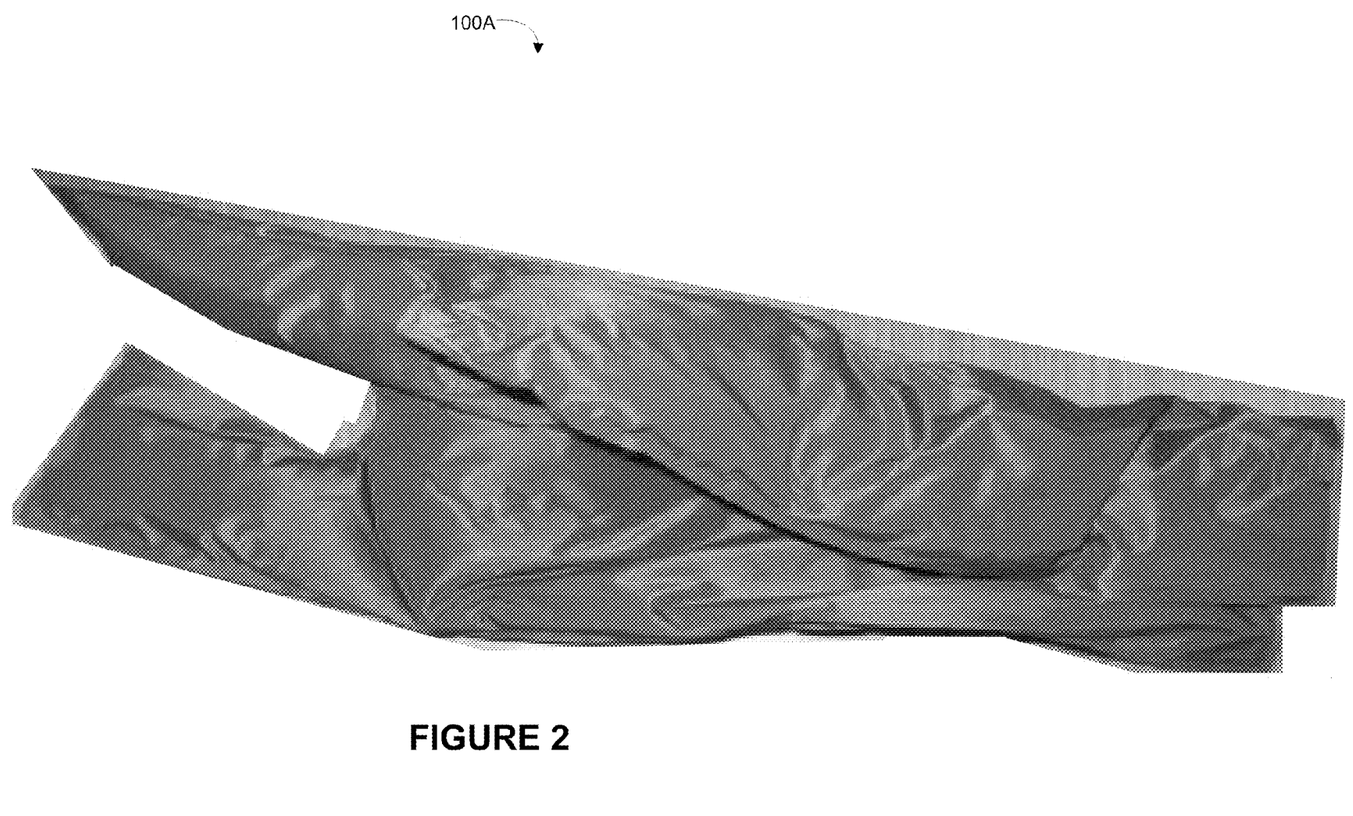
FIG. 2 illustrates a result of first generation splint trial, in accordance with one embodiment of the present invention.
Figure 3:
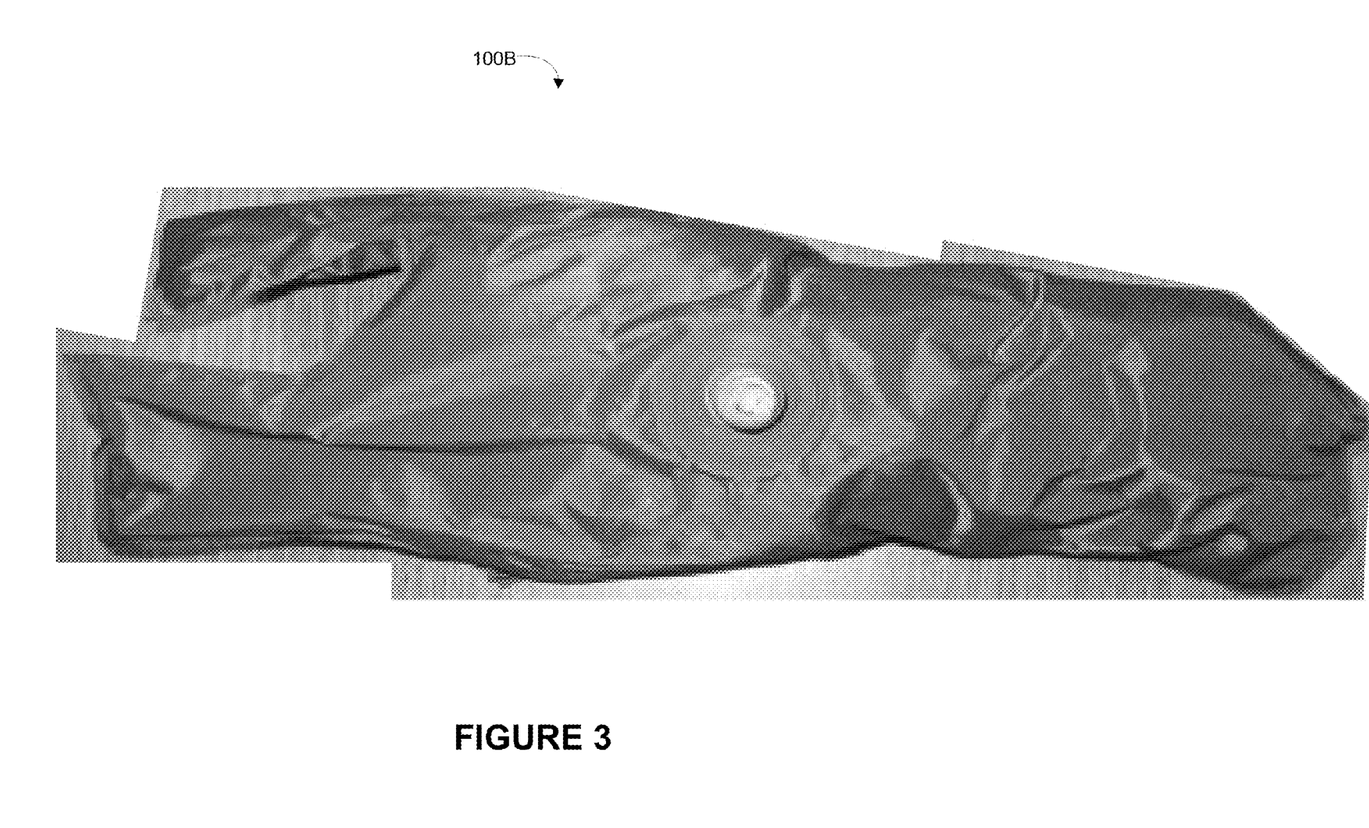
FIG. 3 is a top view of a prototype splint trial, in accordance with one embodiment of the present invention.
Figure 4:
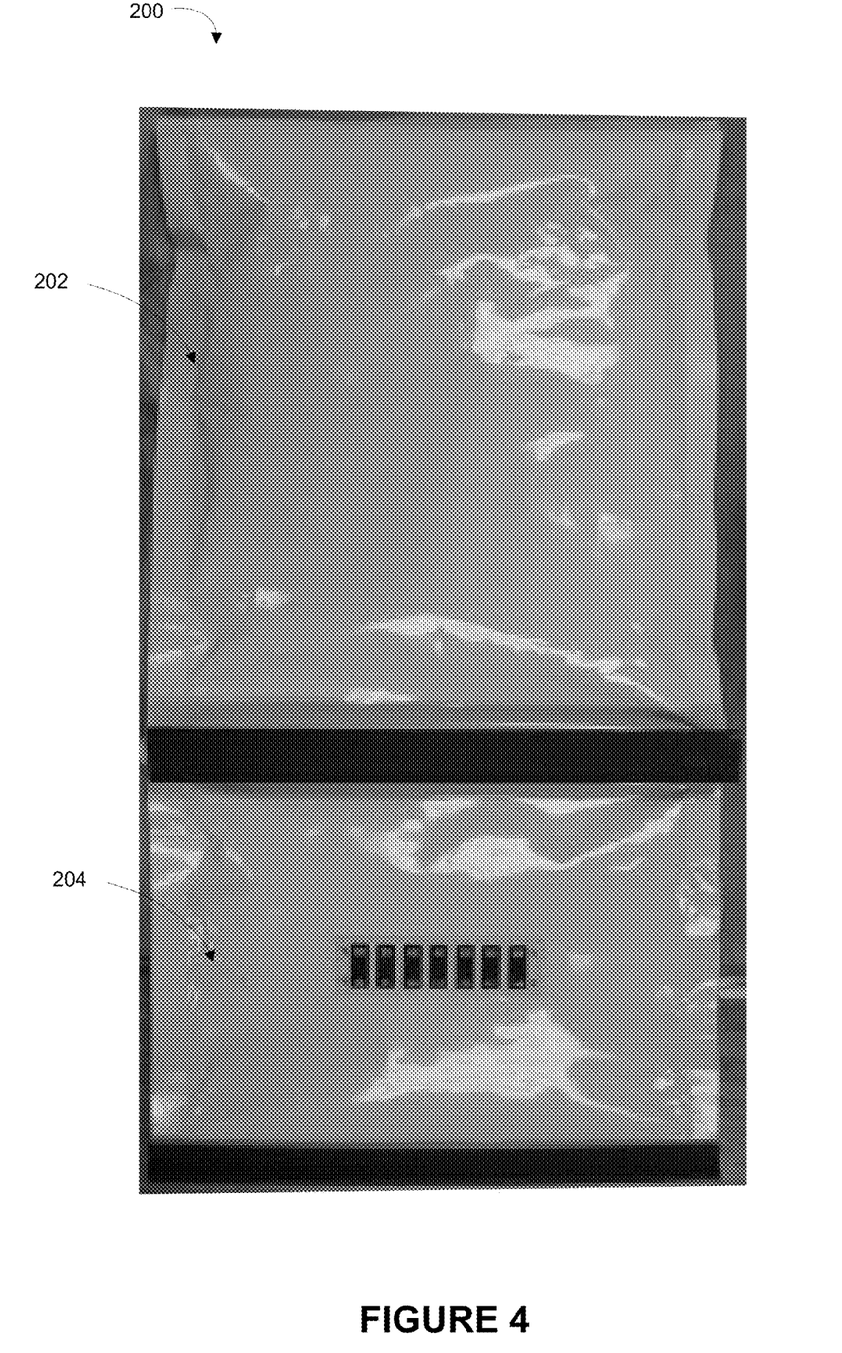
FIG. 4 illustrates a two chambered polymer container, in accordance with one embodiment of the present invention.
Figure 5:
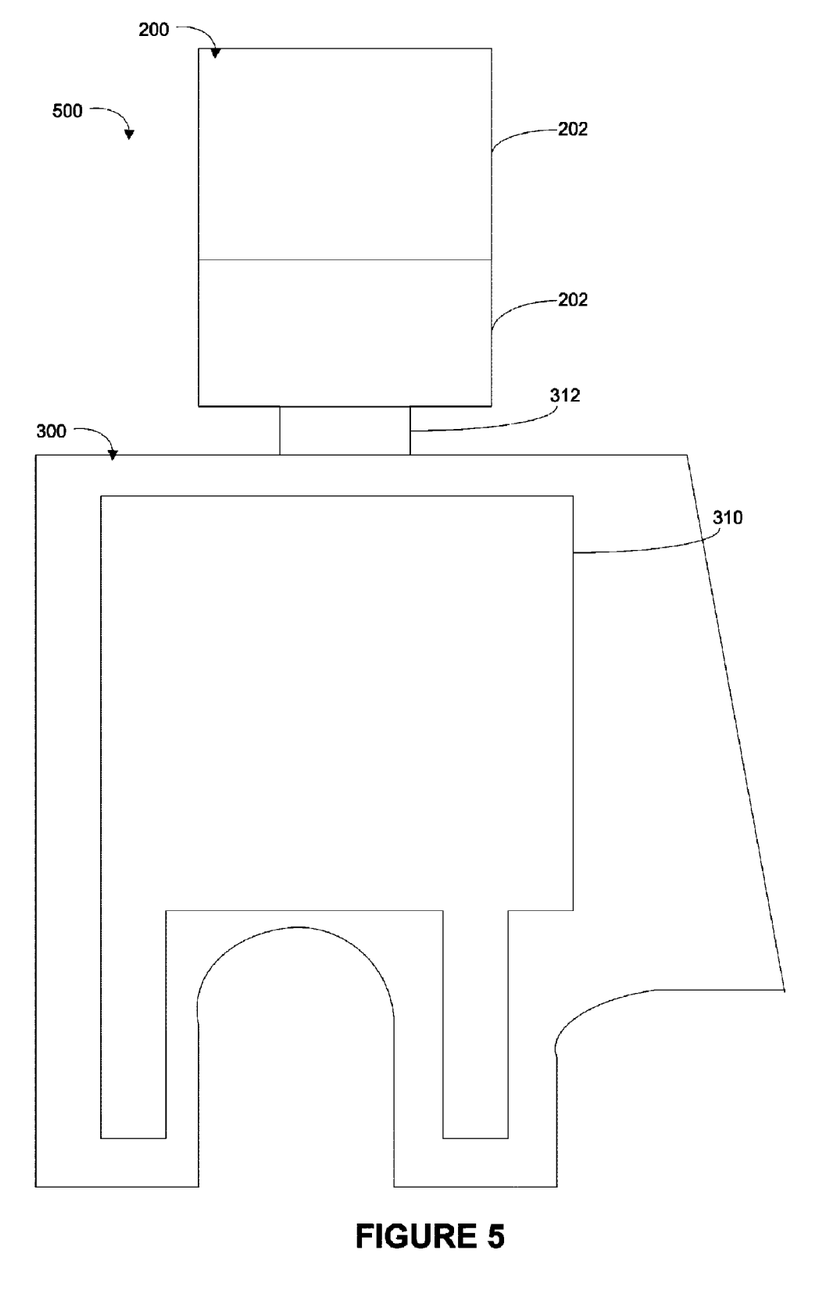
FIG. 5 illustrates a complete prototype, in accordance with one embodiment of the present invention.

We devoted much effort to create the two-part polymer mixture. We found that using a two part mixture consisting of an isocyanate prepolymer based on polymeric 4,4'-methylene bisphenylisocyanate, ethylenediamine tetrakis (propoxylate-block-ethoxylate) tetrol and 2,2,4-trimethyl-1,3-pentanediol-diisobutyrate and a polyol mixture composed of an orthophthalate-diethylene glycol based aromatic polyester polyol, glycerol, and 2,2,4-trimethyl-1,3-pentanediol monoisobutyrate and dibutyltin dialurate as a catalyst produced good results. We tested the first generation prototype 100 as shown in FIGS. 1-3 and concluded it was not satisfactory and that the polymer delivery system 200 was inadequate for practical use. We re-worked to the prototype and polymer delivery system 200 as shown in FIG. 4 and concluded that a bag polymer delivery system 200 could be attached to the polymeric splint 500 as shown in FIG. 5 providing adequate mixing and meeting size constraints. We tested the exotherm of the polymeric splint 500 under cure and found that there is the potential for very high temperatures and that insulation or padding may be added. We also tested the ability of the polymeric splint 500 to accommodate acute swelling, comparing it to the SAM splint (not shown).

2.0 EXPERIMENTATION

2.1 Polymer Development

We developed the polyol component as a mixture of glycerol (a triol), and a polyester polyol which do not readily mix and form more of an emulsion. The mixture was so viscous we chose to use a plasticizer. We selected 2,2,4-trimethyl-1,3-pentanediol monoisobutyrate, which we found not only lowered the viscosity, but also enhanced the mixing and cure because of the hydroxyl functionality of this chemical. We used a various catalyst concentrations, but found that using 0.1% based on total weight of polymer produced very good results (this is approximately 1% by weight of glycerol in the final formulation).

In 20 cm×30 cm mock-ups, we found that we could reliably get adequate hardness in less than 10 minutes. We occasionally had a few samples that it took more than 20 minutes to get rigid. Mixing of the two parts was suspected as being the source of the problem. We decided to try mixing the samples by hand in a cup for various lengths of time: 30 seconds, 45 seconds, and 60 seconds. We determined that the mixing was critical in order to obtain reliable results in cure.

Using the plasticized polyol, we found that 45 seconds of mixing was necessary to obtain the best results. Longer times (60 seconds) resulted in a sticky polymer that could not be spread, but it hardened very quickly.

2.2 Prototype Splint Development

We developed an initial prototype for use as a polymeric splint 100 as shown in FIG. 1: Prototype design for rapid setting polymer splint 100. This polymeric splint 100 was tested using an injection gun (not shown) to deploy the polymer mixture via port 102. We found that the polymer outgassed, foamed vigorously, and was not able to be positioned properly on the arm model. FIGS. 2 and 3 show the results 100A and 100B of the trial.

From this trial we concluded several things: (1) Even if it worked perfectly the size was not quite large enough. (2) It would be better if the splint package were clear, as it was difficult to know if the polymer was uniformly distributed. (3) The polymer delivery system was cumbersome, difficult to use and potentially could expose the user to the uncured polyurethane mixture.

2.3 Second Generation Prototype

With the problems noted in section 2.2, we first changed the polymer delivery system to a two chambered bag polymer delivery system 200 concept. We began by using a bag within a bag concept, and considered the idea of an inner frangible component, but decided there could be a risk of cutting the bag with a fragment to the user which has numerous problems that could result. We settled on a two chambered package polymer delivery system 200 as shown in FIG. 4.

Adequacy of mixing is an issue, but we observed a temperature difference occurs when mixing and are testing the use of a liquid crystal thermometer rather than time of mixing. The outer bag was proposed to be tedlar (poly-vinyl-fluoride), but the manufacturer did not have this material. We chose a chemically similar material (poly-vinyl-chloride) (FIG. 5).

Figure 7:
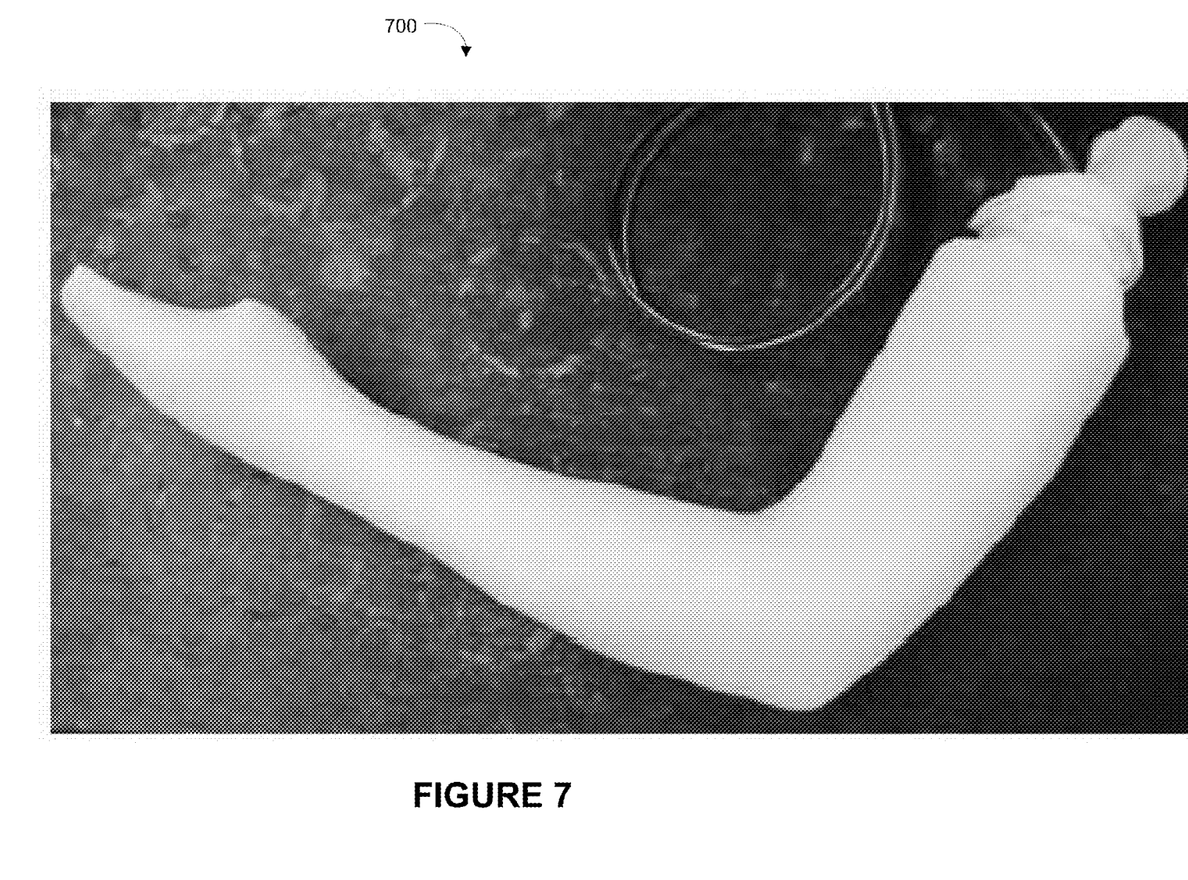
FIG. 7 illustrates a biofidelic arm model used to evaluate splints.

We made five prototypes for initial evaluation. We used 190 grams of polymer mixture which we found to be an insufficient quantity. We used a radius/ulna fracture model 700 as shown in FIG. 7 we made to test the ability of the splint to provide support for a fractured arm. Qualitatively, the polymeric splint 500 provided good support and stabilized the arm model 700 well.

We noted several issues that should be addressed. First, the curing polymer can generate a high temperature (170° F.) if the polymer has a thick spot. Second, the polymer against the skin would be uncomfortable. Third, the rigid composite material can create a pressure point against a bony prominence. For these reasons, we will add padding 310, as shown in FIG. 5, that will be attached to the polymeric splint 500 packaging.

Figure 6A:
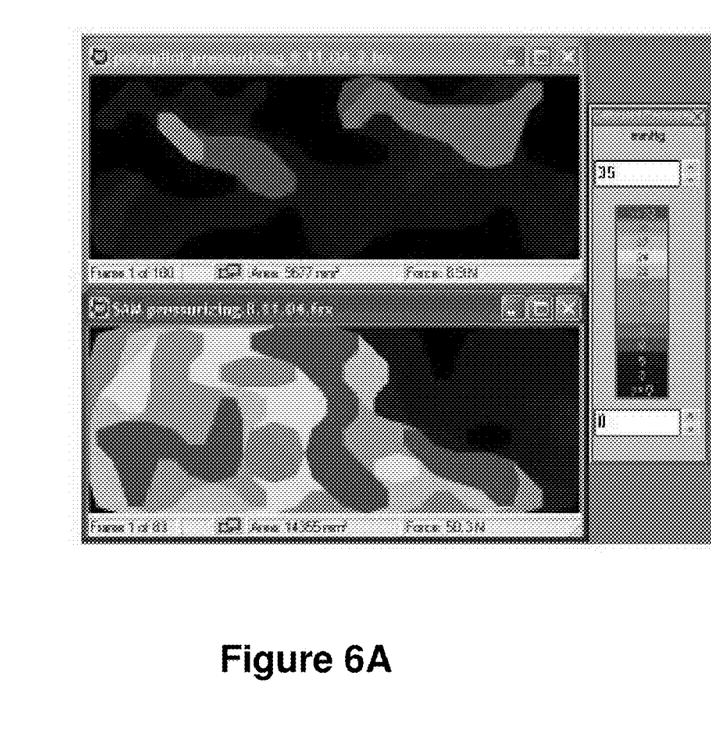
FIGS. 6A and 6B illustrate a comparison of contact pressure by a polymer splint and a SAM splint before and after a simulated acute swelling, in accordance with one embodiment of the present invention.
Figure 6B:
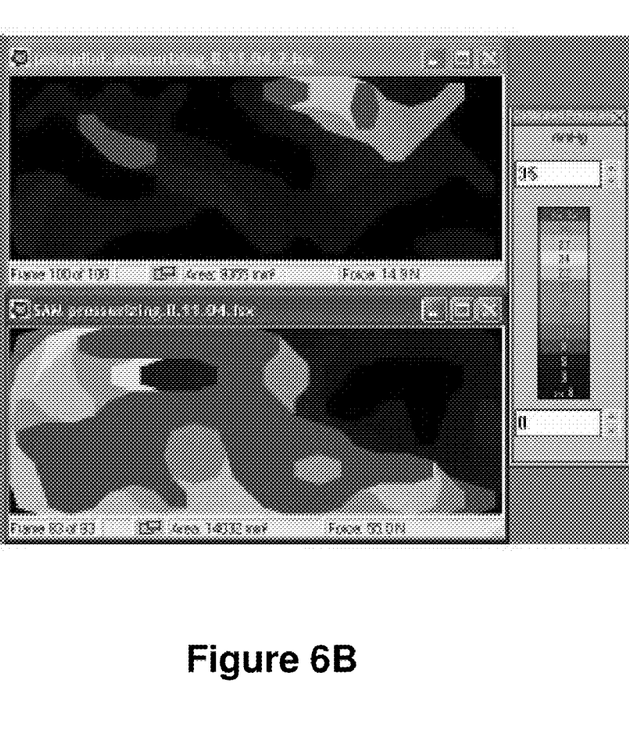

We tested the ability of the splint to accommodate acute swelling against the SAM splint. The SAM splint had a higher mean pressure and a larger area of high pressure compared to the polymeric splint 500 as shown if FIGS. 6A and 6B.

This test suggests that the polymer splint may be better able to accommodate the acute swelling compared to the SAM splint; however, more testing should be done before we can assert that the polymer splint is superior in the aspect of acute swelling.

3.0 RAPID-SETTING POLYURETHANE SPECIFICATIONS

The Rapid-Setting Polyurethane formulations described herein can:

Cure rapidly under thin film conditions (e.g., less than about ⅛ inch)

Use an isocyanate prepolymer based on polymeric 4,4'-methylene bisphenylisocyanate, ethylenediamine tetrakis (propoxylate-block-ethoxylate) tetrol and 2,2,4-trimethyl-1,3-pentanedioldiisobutyrate as Part A of a 2-part mixture Use an orthophthalate-diethylene glycol based aromatic polyester polyol, glycerol, and 2,2,4-trimethyl-1,3-pentanediol monoisobutyrate as Part B of a 2-part mixture Have a high hardness—rated at Shore A 80-85 with a high density foam (0.4 g/cc).

3.1 Splint Polyurethane Method

Part A:

An isocyanate prepolymer (Part A) is prepared using 67.4% polymeric 4,4'-methylene bisphenylisocyanate 27.0% ethylenediamine tatrakis (propoxylate-block-ethoxylate) tetrol ~3600 MW and 5.6% 2,2,4-trimethyl-1,3-pentanediol diisobutyrate.

Preparation of Part A—Isocyanate Prepolymer

The polymeric 4,4'-methylene bisphenylisocyanate is placed in a vacuum flask and degassed at 1 mm Hg for 10-20 minutes while stirring until bubbling has substantially decreased. The ethylenediamine-based tetrol and 2,2,4-trimethyl-1,3-pentanediol diisobutyrate are then added and the mixture is rapidly stirred for 10 minutes until a uniform brown color.

Part B:

A polyol mixture is prepared using 47.2% glycerol containing 1% dibutyltin dilaurate, 23.6% orthophthalate-diethylene glycol based aromatic polyester polyol and 29.2% 2,2,4-trimethyl-1,3-pentanediol monoisobutyrate.

Preparation of Part B—Polyol Mixture

The glycerol containing 1% dibutyltin dilaurate is combined with the orthophthalate-diethylene glycol based aromatic polyester polyol and 2,2,4-trimethyl-1,3-pentanediol monoisobutyrate and mixed while stirring for 20 minutes.

Preparation of Rigid Foam

Parts A and B are combined in a 3.75:1 ratio by weight, mixed well for 45 seconds, add applied uniformly to the splint.

Alternate Formulations

Formulations omitting the 2,2,4-trimethyl-1,3-pentanediol diisobutyrate and 2,2,4-trimethyl-1,3-pentanediol monoisobutyrate also reacted to form hard foams with increased viscosity.

Formulations with lower levels of dibutyltin dilaurate increased curing time. Higher levels of dibutylin dilaurate had no effect.

Formulations using only orthophthalate-diethylene glycol based aromatic polyester polyol as the polyol also increased curing time to appropriate hardness.

Formulations using mixtures of orthophthalate-diethylene glycol based aromatic polyester polyol and glycerol propoxylate (Mn ~0.725) as the polyols also increased curing time and had higher mix viscosities.

Formulations using only polymeric 4,4'-methylene bisphenylisocyanate as the isocyanate prepolymer had higher mix viscosities, were slower to react to full hardness, and presented a higher risk of free isocyanate exposure.

A Rapid Setting Polymeric Splint for Use in Tactical Environments

Introduction.

It has been estimated that extremity trauma accounts for as much as 50 percent of all wartime injuries. While fractures are not necessarily fatal, they significantly impair the ability of the soldier to perform tasks. If not properly treated, permanent damage to sensory function, range of motion, or mobility can occur, or in the worst case, a limb may require amputation. Open fractures tend to be more common since the injuries are often associated with projectile penetration due to direct-fire weapons, AP mines, or exploding ordinance. The profuse bleeding, aseptic environment, and other factors in addition to fractures significantly influence the need for rapid, effective management of injuries. Current management of fractures in tactical environments are generally field expedient measures, which provide adequate, but sub-optimal treatment. The goal of this research was to develop and evaluate a rapid setting polymeric splint 500 using advanced composite materials to create an easily applied polymeric splint 500 that provides superior stability compared to other expedient measures.

A two-part polyurethane was developed to be used with a high performance fiber fabric.

Figure 8A:
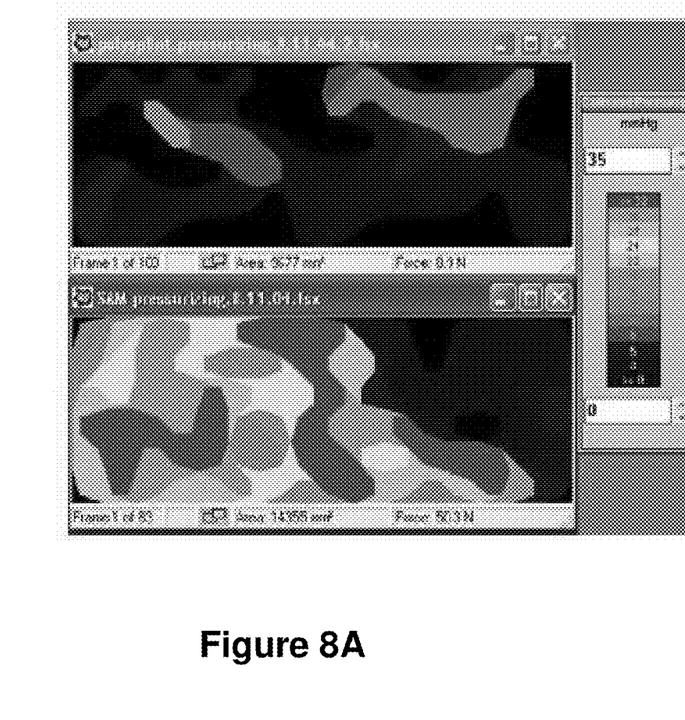
FIGS. 8A and 8B illustrate a comparison of contact pressure by a polymer splint and a SAM splint before and after a simulated acute swelling, in accordance with one embodiment of the present invention.
Figure 8B:
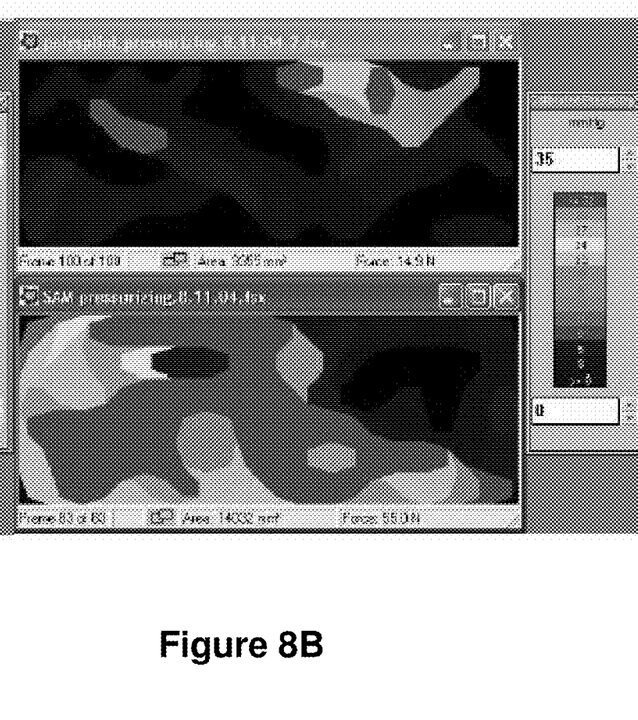

Exotherm of the polymer during the chemical reaction was measured using a scanning thermometer was used to using a set of twelve Type T thermocouples of both probe and surface mount style. The sensors were attached to a biofidelic arm which includes a pair of water inflatable bladders that can pressurized by using tubing that is run out of the arm model 700 as shown in FIG. 7. FIGS. 8a and 8B are graphical representations of the surface contact pressures before and after, respectively, simulated acute swelling were measured using Tekscan. We chose 35 mmHg as a baseline for tolerable surface pressure. Comparisons between the SAM splint graphs and the polymeric splint 500 graphs were performed to test the ability to accommodate acute swelling.

The working time of the polymer is approximately 45 seconds with set occurring in about 5 minutes. The hardness of the polymer ranges from 60 to 85 shore A. Peak exotherm temperatures are generally around 120° F., but occasionally can be quite high, reaching near 170° F. The splint accommodates simulated acute swelling with no significant change is surface pressure distribution. The peak surface pressure for the polymeric splint was 114 mmHg isolated to one 5 mm×5 mm sensel, with the vast majority of the area being less than 35 mmHg (FIGS. 8A and 8B). There were 3 sensels where the change in pressure was greater than 35 mmHg. The resultant force acting on the sensor area was 14.9 N. For the SAM splint, the peak pressure was 126 mmHg, over 2 sensels with the resultant force acting over the sensor area being 55 N.

Approximately half of the SAM splint measured pressure area was greater than 35 mmHg during the simulated acute swelling.

The polymeric splint 500 shows good promise of being able to function as a splint in tactical environments. Being self-contained and conforming provides the field medic with an easy to use, safe and effective means for immobilizing a fractured extremity (e.g., leg, foot, ankle, arm, neck, or other item to be supported). While the high exothermic temperature is not always observed, the occasional high exotherm temperature, insulation or padding 310 may also be included, which is to be part of the polymeric splint 500 design and will provide comfort to the user.

We have only run a small number of trials comparing the SAM Splint to the polymeric splint 500 (N=3), therefore, we are not as yet prepared to make definitive statements about the specific advantages of one splint over another. The advantage to the SAM splint is that it is easily applied, very light weight, does not have an exotherm and can be used in any environment and has been used in field environments. Our initial results suggest, however, that the SAM Splint does not accommodate acute swelling well. This could be alleviated by releasing the SAM splint periodically and thus avoiding potential compartment syndrome. The polymeric splint 500, however, may better accommodate the acute swelling event. The polymeric splint 500 is fully conforming, requiring no additional items to support to the limb. As a conforming splint, the polymeric splint 500 should better distribute loads across the surface of the injured limb (e.g., leg, foot, ankle, arm, neck, or other item to be supported).

The polymeric splint 500 is durable, rigid and easily removed with a cast saw. While the polymeric splint 500 has not yet been evaluated for lower extremities, the splint would probably function well for tibial as well as foot and ankle fractures, although if not likely to be able to provide sufficient support to allow weight bearing. The splint would most likely be inadequate for femoral fractures.

One embodiment of the present invention provides a polymeric splint 500 that includes a first container 300 capable of being wrapped about an item (e.g., leg, foot, ankle, arm, neck, etc.) to be supported. A second container 200 capable of containing a two part mixture during a mixing operation. The second container 200 can be incorporated into or be separate from the first container 300. The second container 200 is capable of delivering the mixture into the first container 300. The second container 200 may be removable coupled to the first container 300.

The mixture hardens to form a support structure. The hardened mixture can have a hardness of from about 60 to about 85 Shore A. The mixture can include a polymer. The mixture can include a rapid setting polyurethane (e.g., setting in about five minutes or less).

One embodiment of the present invention includes a method of using the polymeric splint 500 that includes the following operations: Mixing the polyurethane in the 2-chambered container 200, forcing the mixture into the first container 300 (e.g., pressing on the 2-chambered container 200 to cause the mixture to flow from the 2-chambered container and into the first container 300.) Wrapping the polymeric splint 500 (e.g., filled first container 300) about the item to be splinted (e.g., injured extremity, leg, arm, neck, or other item to be supported.) Hold polymeric splint 500 in place until the mixture hardens in the polymeric splint 500.

It will be appreciated that the instructions represented by the operations in the above figures are not required to be performed in the order illustrated, and that all the processing represented by the operations may not be necessary to practice the invention.

Although the foregoing invention has been described in some detail for purposes of clarity of understanding, it will be apparent that certain changes and modifications may be practiced within the scope of the appended claims. Accordingly, the present embodiments are to be considered as illustrative and not restrictive, and the invention is not to be limited to the details given herein, but may be modified within the scope and equivalents of the described embodiments.

What is claimed is:

1. A method of using a conforming polymeric splint including:
   moving at least one of a plurality of polyurethane components from a first chamber of a 2-chambered container into second chamber of the 2-chambered container, the second chamber containing a remaining ones of the plurality of polyurethane components;
   mixing the plurality of polyurethane components in the second chamber;
   placing the mixture into the splint, wherein the splint is a first container coupled to one of the chambers of the 2-chambered container;
   forming the first container about a body part to be supported and immobilized by the conforming splint to form the conforming polymeric splint; and
   holding the conforming polymeric splint in place until the mixture hardens to form a one piece support structure about the supported and immobilized body part and wherein the support structure accommodates acute swelling in the supported and immobilized body part.

2. The method of claim 1, wherein placing the mixture into the splint includes applying pressure on the 2-chambered container to cause the mixture to flow from the 2-chambered container and into the first container.

3. The method of claim 1, wherein the hardened mixture can have a hardness of from about 60 to about 85 Shore A.

4. The method of claim 1, wherein the mixture includes a polymer.

5. The method of claim 1, wherein the mixture includes a polyurethane capable of setting in less than about five minutes.

6. The method of claim 1, wherein the first chamber is incorporated into the second chamber.

7. The method of claim 1, wherein the support structure includes a layer a padding between the support structure and the supported and immobilized body part.

* * * * *